US012357505B2

(12) United States Patent
Gliner et al.

(10) Patent No.: US 12,357,505 B2
(45) Date of Patent: Jul. 15, 2025

(54) ANTI-VACUUM SURGE SYSTEM

(71) Applicant: JOHNSON & JOHNSON SURGICAL VISION, INC., Irvine, CA (US)

(72) Inventors: Vadim Gliner, Haifa (IL); Alon Boumendil, Givat Nili (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 843 days.

(21) Appl. No.: 17/511,166

(22) Filed: Oct. 26, 2021

(65) Prior Publication Data
US 2023/0125462 A1    Apr. 27, 2023

(51) Int. Cl.
*A61F 9/007* (2006.01)
*A61M 1/00* (2006.01)

(52) U.S. Cl.
CPC .......... *A61F 9/00745* (2013.01); *A61M 1/73* (2021.05); *A61M 1/743* (2021.05); *A61B 2217/005* (2013.01); *A61M 2205/3344* (2013.01)

(58) Field of Classification Search
CPC ..... A61F 9/00745; A61M 1/73; A61M 1/743; A61M 2205/3344; A61B 2217/005
See application file for complete search history.

(56) References Cited

U.S. PATENT DOCUMENTS

| 6,159,175 | A | 12/2000 | Strukel et al. |
|---|---|---|---|
| 8,721,594 | B2 | 5/2014 | Zacharias |
| 10,940,039 | B2 | 3/2021 | Banko |
| 2008/0319374 | A1* | 12/2008 | Zacharias ............. A61M 1/743 604/22 |
| 2014/0257172 | A1 | 9/2014 | Yalamanchili |
| 2019/0133822 | A1* | 5/2019 | Banko ................... A61M 1/774 |
| 2019/0143008 | A1 | 5/2019 | Brundage et al. |

OTHER PUBLICATIONS

Saalbach, et al., Self-sensing cavitation detection in ultrasound-induced acoustic cavitation, Ultrasonics 94 (2019), 401-410.

* cited by examiner

*Primary Examiner* — Erin McGrath

(57) ABSTRACT

In one embodiment, a phacoemulsification system includes a phacoemulsification probe configured to be inserted into an eye, and including a needle, a horn configured to support the needle, and an ultrasonic actuator connected to the horn and configured to vibrate the needle to emulsify a lens of the eye, an aspiration line partially disposed in the needle, a pumping sub-system connected to the aspiration line and configured to remove fluid and waste matter from the eye via the aspiration line, a valve disposed in the aspiration line and configured to control fluid connectivity in the aspiration line, a sensor configured to provide a signal indicative of a fluid metric in the aspiration line, and a controller configured to find an activation status of the ultrasonic actuator, and selectively control the valve responsively to the fluid metric and the activation status of the ultrasonic actuator.

18 Claims, 10 Drawing Sheets

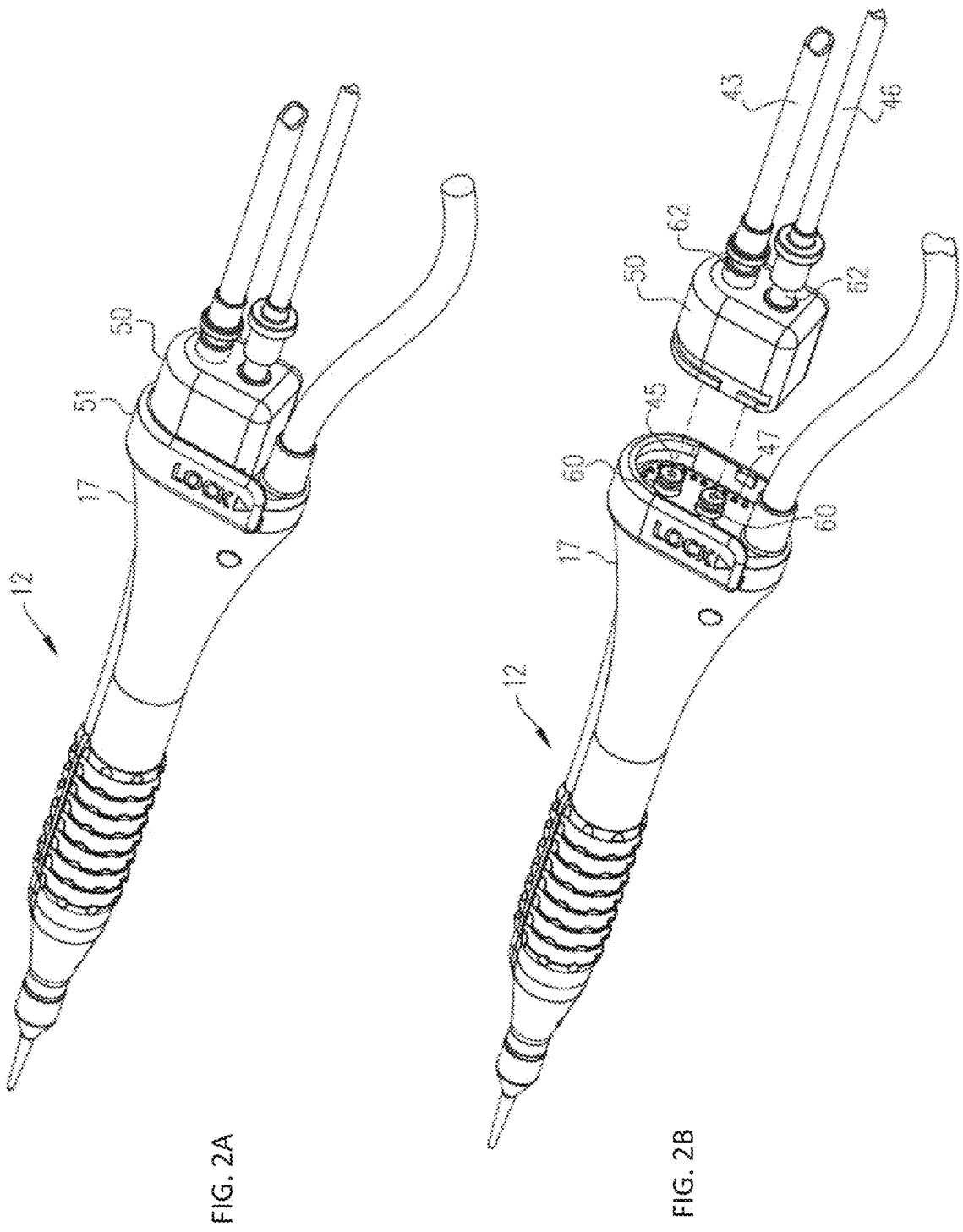

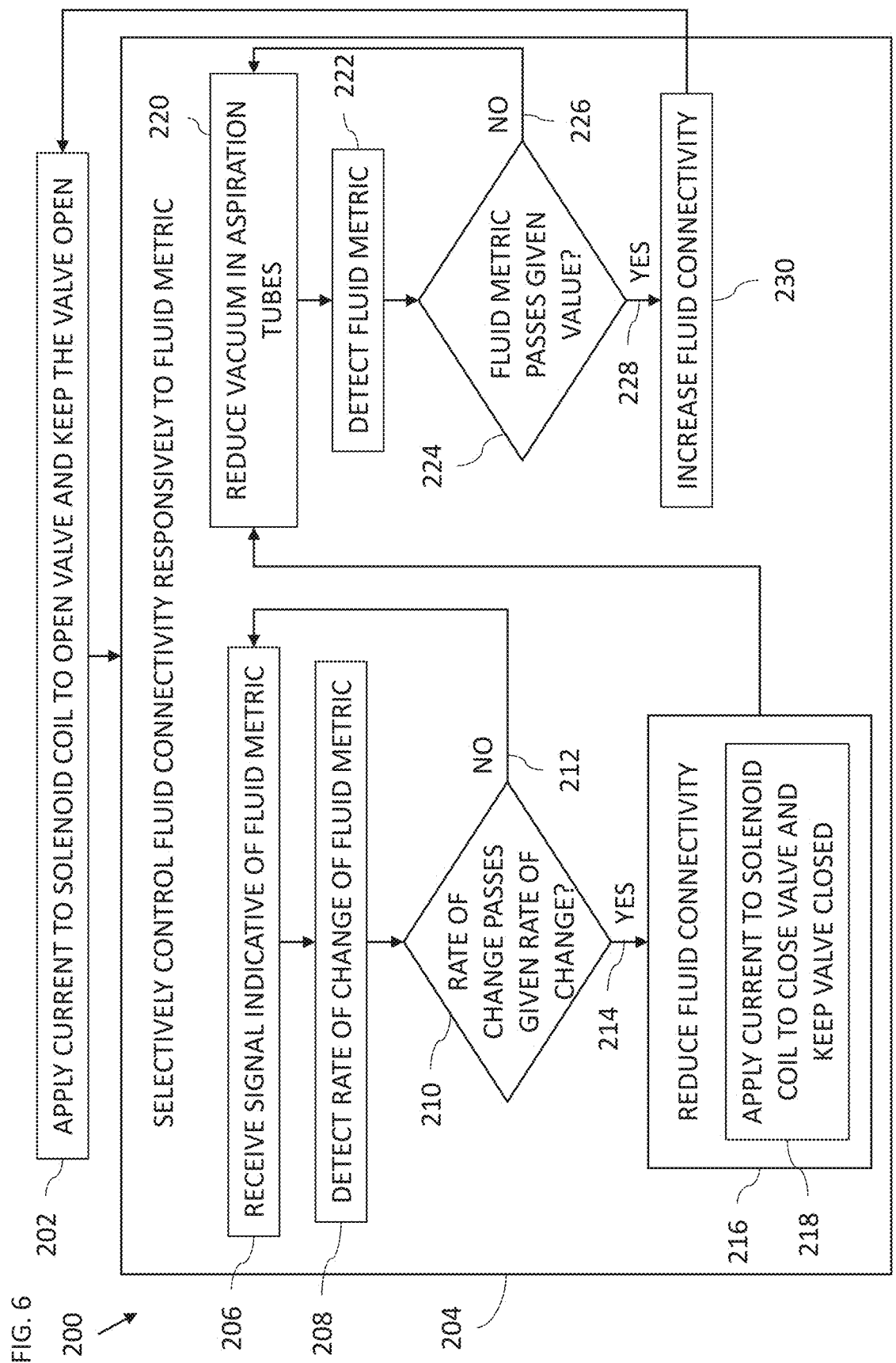

ANTI-VACUUM SURGE SYSTEM

FIELD OF THE INVENTION

The present invention relates to medical systems, and in particular, but not exclusively to, fluid dynamics in medical systems.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution (BSS) to maintain the anterior chamber of the eye. After removing the cataract with phacoemulsification, the softer outer lens cortex is removed with suction. An intraocular lens (IOL) is then introduced into the empty lens capsule restoring the patient's vision.

SUMMARY

There is provided in accordance with still another embodiment of the present disclosure, a phacoemulsification system, including a phacoemulsification probe configured to be inserted into an eye, and including a needle, a horn configured to support the needle, and an ultrasonic actuator coupled with the horn and configured to vibrate the needle to emulsify a lens of the eye, an aspiration line partially disposed in the needle, a pumping sub-system connected to the aspiration line and configured to remove fluid and waste matter from the eye via the aspiration line, a valve disposed in the aspiration line and configured to control fluid connectivity in the aspiration line, a sensor configured to provide a signal indicative of a fluid metric in the aspiration line, and a controller configured to find an activation status of the ultrasonic actuator, and selectively control the valve responsively to the fluid metric and the activation status of the ultrasonic actuator.

Further in accordance with an embodiment of the present disclosure the controller is configured to selectively control the valve to restrict fluid flow along the aspiration line responsively to the fluid metric and the activation status of the ultrasonic actuator.

Still further in accordance with an embodiment of the present disclosure the controller is configured to selectively control the valve to restrict fluid flow along the aspiration line responsively to the activation status of the ultrasonic actuator being equal to active and the fluid metric being indicative of an occlusion or a post-occlusion surge.

Additionally in accordance with an embodiment of the present disclosure the fluid metric is a pressure metric, and the sensor includes a pressure sensor configured to sense the pressure metric in the aspiration line.

Moreover, in accordance with an embodiment of the present disclosure the controller is configured to selectively control the valve to restrict fluid flow along the aspiration line responsively to the activation status of the ultrasonic actuator being equal to active and a rate of change of the pressure metric in the aspiration line exceeding a threshold value.

Further in accordance with an embodiment of the present disclosure the controller is configured to detect cavitation caused by vibration of the needle responsively to the signal provided by the sensor, and find the activation status of the ultrasonic actuator responsively to detecting the cavitation.

Still further in accordance with an embodiment of the present disclosure the sensor includes a pressure sensor configured to sense pressure in the aspiration line, and the controller is configured to detect the cavitation caused by the vibration of the needle responsively to pressure fluctuations sensed by the pressure sensor.

Additionally in accordance with an embodiment of the present disclosure the controller is configured to compute a signal-to-noise ratio responsively to the signal provided by the sensor, and detect the cavitation responsively to the computed signal-to-noise ratio.

Moreover, in accordance with an embodiment of the present disclosure the controller is configured to selectively control the valve to restrict fluid flow along the aspiration line responsively to the activation status of the ultrasonic actuator being equal to active and a rate of change of the pressure metric sensed by the pressure sensor exceeding a threshold value.

There is also provided in accordance with another embodiment of the present disclosure, a phacoemulsification method, including inserting a phacoemulsification probe into an eye, vibrating a needle of the phacoemulsification probe to emulsify a lens of the eye, removing fluid and waste matter from the eye via an aspiration line partially disposed in the needle, control fluid connectivity in the aspiration line using a valve, providing a signal indicative of a fluid metric in the aspiration line, and finding an activation status of an ultrasonic actuator which selectively vibrates the needle, and selectively controlling the valve responsively to the fluid metric and the activation status of the ultrasonic actuator.

Further in accordance with an embodiment of the present disclosure the selectively controlling includes selectively controlling the valve to restrict fluid flow along the aspiration line responsively to the fluid metric and the activation status of the ultrasonic actuator.

Still further in accordance with an embodiment of the present disclosure the selectively controlling includes selectively controlling the valve to restrict fluid flow along the aspiration line responsively to the activation status of the ultrasonic actuator being equal to active and the fluid metric being indicative of an occlusion or a post-occlusion surge.

Additionally in accordance with an embodiment of the present disclosure the fluid metric is a pressure metric, the method further includes sensing the pressure metric in the aspiration line.

Moreover, in accordance with an embodiment of the present disclosure the selectively controlling includes selectively controlling the valve to restrict fluid flow along the aspiration line responsively to the activation status of the ultrasonic actuator being equal to active and a rate of change of the pressure metric in the aspiration line exceeding a threshold value.

Further in accordance with an embodiment of the present disclosure, the method includes detecting cavitation caused by vibration of the needle responsively to the signal provided by the sensor, and wherein the finding includes finding the activation status of the ultrasonic actuator responsively to detecting the cavitation.

Still further in accordance with an embodiment of the present disclosure, the method includes sensing pressure in the aspiration line, and wherein the detecting includes detecting the cavitation caused by the vibration of the needle responsively to sensed pressure fluctuations.

Additionally in accordance with an embodiment of the present disclosure, the method includes computing a signal-to-noise ratio responsively to the provided signal, and wherein the detecting includes detecting the cavitation responsively to the computed signal-to-noise ratio.

Moreover, in accordance with an embodiment of the present disclosure the selectively controlling includes selectively controlling the valve to restrict fluid flow along the aspiration line responsively to the activation status of the ultrasonic actuator being equal to active and a rate of change of a sensed pressure metric exceeding a threshold value.

BRIEF DESCRIPTION OF THE DRAWINGS

The present invention will be understood from the following detailed description, taken in conjunction with the drawings in which:

FIGS. 2A-B are views of a probe for use with the system of FIG. 1;

FIG. 6 is a flowchart including steps in a method of operation of the system of FIG. 1;

DESCRIPTION OF EXAMPLE EMBODIMENTS

Overview

Figure 1:
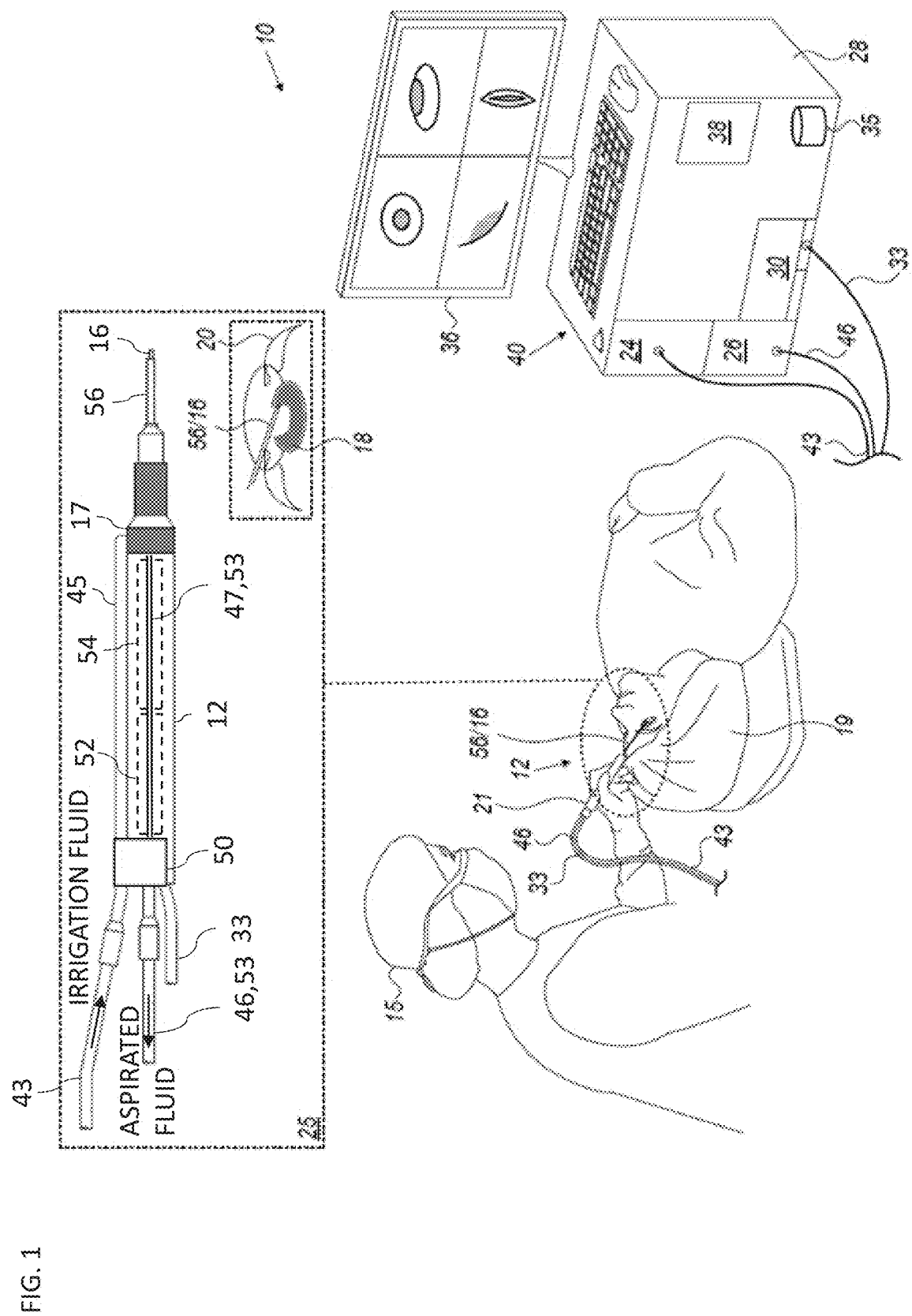
FIG. 1 is a partly pictorial, partly block diagram view of a phacoemulsification system constructed and operative in accordance with an embodiment of the present invention.

During phacoemulsification of an eye lens, the emulsified lens particles are aspirated. When a particle blocks the inlet of an aspiration channel (which could be in a needle of a phacoemulsification probe) causing occlusion of the channel, the vacuum in the channel increases. When the channel becomes unblocked (e.g., by the particle being subsequently sucked down the channel), the high vacuum in the channel causes an aspiration surge known as a post occlusion surge, which may have traumatic consequences to the eye. For example, sensitive parts of the eye may be damaged or come into contact with the needle of the phacoemulsification probe.

A possible solution to the problem of vacuum level surge is incorporating an aspiration bypass. Such a bypass may consist of a small hole or channel between an irrigation channel of the probe and the aspiration channel. When a blockage occurs, the high vacuum diverts irrigation fluid into the aspiration channel via the hole, thereby limiting the vacuum level.

However, the above-described bypass aspiration technique is still prone to produce a traumatic aspiration surge when the channel unblocks, since the high vacuum is present in a long tube (which being flexible may also be compressed adding to the vacuum problem) between a portion of the aspiration channel inside the emulsification probe and the aspiration pump, and that large, partially vacant volume, may therefore cause a surge when the occlusion breaks. Moreover, diversion of irrigation fluid may cause an uncontrolled pressure-drop in the irrigation channel, which may also pose a risk to the eye.

One solution includes removing or reducing the pressure difference in the aspiration channel during the occlusion clearance. An anti-vacuum surge (AVS) system including a valve, e.g., a fast-acting and programmable solenoid valve, may restrict or block fluid connectivity in the aspiration channel during occlusion clearance based on detection of a sharp change in pressure in the aspiration channel. The vacuum can then be reduced in a controlled manner until an acceptable pressure is achieved, allowing the valve to be opened again. The valve may include a solenoid coil which moves a plunger including a permanent magnet in a valve cavity.

The AVS system is generally constantly operational, and closes the valve on detection of a sharp change in pressure even if the phacoemulsification needle is not being vibrated and there is a low risk associated with the needle damaging the eye. The constant operation of the AVS system may however be undesirable when the physician is trying to build up a vacuum in the aspiration line as fast as possible, for example, to grab a particle, even when the phacoemulsification needle is not vibrating. To add to this problem, there is a general data disconnection between the activation of the needle and the operation of the AVS such that direct feedback regarding the needle operation may not be available to the AVS.

Embodiments of the present invention solve the above problems by only activating the valve of the AVS system (e.g., according to a sharp change (e.g., rate of change) in pressure or other fluid metric) during a time period when the needle is being vibrated thereby allowing such activities as the physician to build up a vacuum in the aspiration line as fast as possible, for example, to grab a particle when the phacoemulsification needle is not vibrating.

When the needle is vibrated, the needle causes cavitation (bubbles) which leads to high frequency pressure fluctuations in the aspiration line. The vibration of the needle may therefore be detected according to the level of cavitation in the aspiration line. In some embodiments, the cavitation is detected based on detecting pressure fluctuations in the aspiration line. The pressure level in the aspiration line may be sensed by a pressure sensor of the AVS system.

In some embodiments, high frequency pressure fluctuations in the aspiration line indicative of cavitation, and therefore indicative that the needle is being vibrated, may be detected by computing a signal to noise ratio (SNR) of the pressure signal provided by the sensor. If the SNR is greater than a given threshold, for example, the noise power is greater than 5% of the signal power, the needle may be assumed to be vibrating causing cavitation.

System Description

Reference is now made to FIG. 1 that is a partly pictorial, partly block diagram view of a phacoemulsification system 10 constructed and operative in accordance with an embodiment of the present invention.

The phacoemulsification system 10 comprises a phacoemulsification probe 12 (e.g., handpiece). In some embodiments, the phacoemulsification probe 12 may be replaced by any suitable medical tool. As seen in the pictorial view of phacoemulsification system 10, and in inset 25, phacoemulsification probe 12 comprises a needle 16, a probe body 17, and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, irrigation sleeve 56 may have one or more side ports at, or near, the distal end to allow irrigation fluid to flow towards the distal end of the phacoemulsification probe 12 through the fluid pathway and out of the port(s).

The needle 16 of the phacoemulsification probe 12 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, CA, USA.

In the embodiment of FIG. 1, during the phacoemulsification procedure, a pumping sub-system 24 comprised in a console 28 pumps irrigation fluid from an irrigation reservoir (not shown) to the irrigation sleeve 56 to irrigate the eye 20. The irrigation fluid is pumped via an irrigation tubing line 43 running from the console 28 to an irrigation channel 45 of probe 12, the distal end of the irrigation channel 45 including the fluid pathway in the irrigation sleeve 56. The irrigation tubing line 43 is typically flexible and may be prone to collapsing during an occlusion of the needle 16. In another embodiment, the pumping sub-system 24 may be coupled or replaced with a gravity fed irrigation source such as a BSS bottle/bag.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle in the console 28. The aspiration is affected by a pumping sub-system 26, also comprised in console 28. The aspiration tubing line 46 and the aspiration channel 47 are described herein as an aspiration line 53. The aspiration line 53 is therefore partially disposed in the needle 16 and is connected to the pumping sub-system 26, which is configured to remove the fluid and waste matter from the eye 20 via the aspiration line 53.

System 10 may include a fluid dynamics cartridge 50 (which in an embodiment, may be removable), which may include one or more valves to regulate the flow of fluid in the irrigation channel 45 and/or aspiration channel 47 as well as sensors, described in more detail with reference to FIGS. 2A-6. Part of the irrigation channel 45 and the aspiration channel 47 is disposed in the probe body 17 and part is disposed in the cartridge 50.

Phacoemulsification probe 12 includes other elements, such as an ultrasonic actuator 52, e.g., piezoelectric crystal, coupled with a horn 54 configured to support the needle 16 and drive vibration of needle 16 to emulsify the lens of the eye 20. The ultrasonic actuator 52 is configured to vibrate needle 16 in a resonant vibration mode. The vibration of needle 16 is used to break a cataract into small pieces during a phacoemulsification procedure. Console 28 comprises an ultrasonic (e.g., piezoelectric) drive module 30, coupled with the ultrasonic actuator 52, using electrical wiring running in a cable 33. Drive module 30 is controlled by a controller 38 and conveys processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47, as described in more detail with reference to FIG. 6. In some embodiments, at least some of the functionality of the controller 38 may be implemented using a controller disposed in the phacoemulsification probe 12 (e.g., the cartridge 50).

Controller 38 may receive user-based commands via a user interface 40, which may include setting a vibration mode and/or frequency of the ultrasonic actuator 52, and setting or adjusting an irrigation and/or aspiration rate of the pumping sub-systems 24/26. In some embodiments, user interface 40 and a display 36 may be combined as a single touch screen graphical user interface. In some embodiments, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two. In some embodiments, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Reference is now made to FIGS. 2A-B, which are views of the phacoemulsification probe 12 for use with the system 10 of FIG. 1. FIG. 2A shows the cartridge 50, which is configured to be reversibly attached (using a clip 51) to the probe body 17 of the phacoemulsification probe 12. FIG. 2B shows the cartridge 50 detached from the probe body 17. FIG. 2B shows ports 60 of the irrigation channel 45 and the aspiration channel 47 on the probe body 17 for connecting with corresponding ports (not shown in FIG. 2B, but shown in FIG. 3A) of the cartridge 50. FIG. 2B also shows irrigation tubing line 43 and aspiration tubing line 46 connected to ports 62 of the cartridge 50.

Figure 3A:
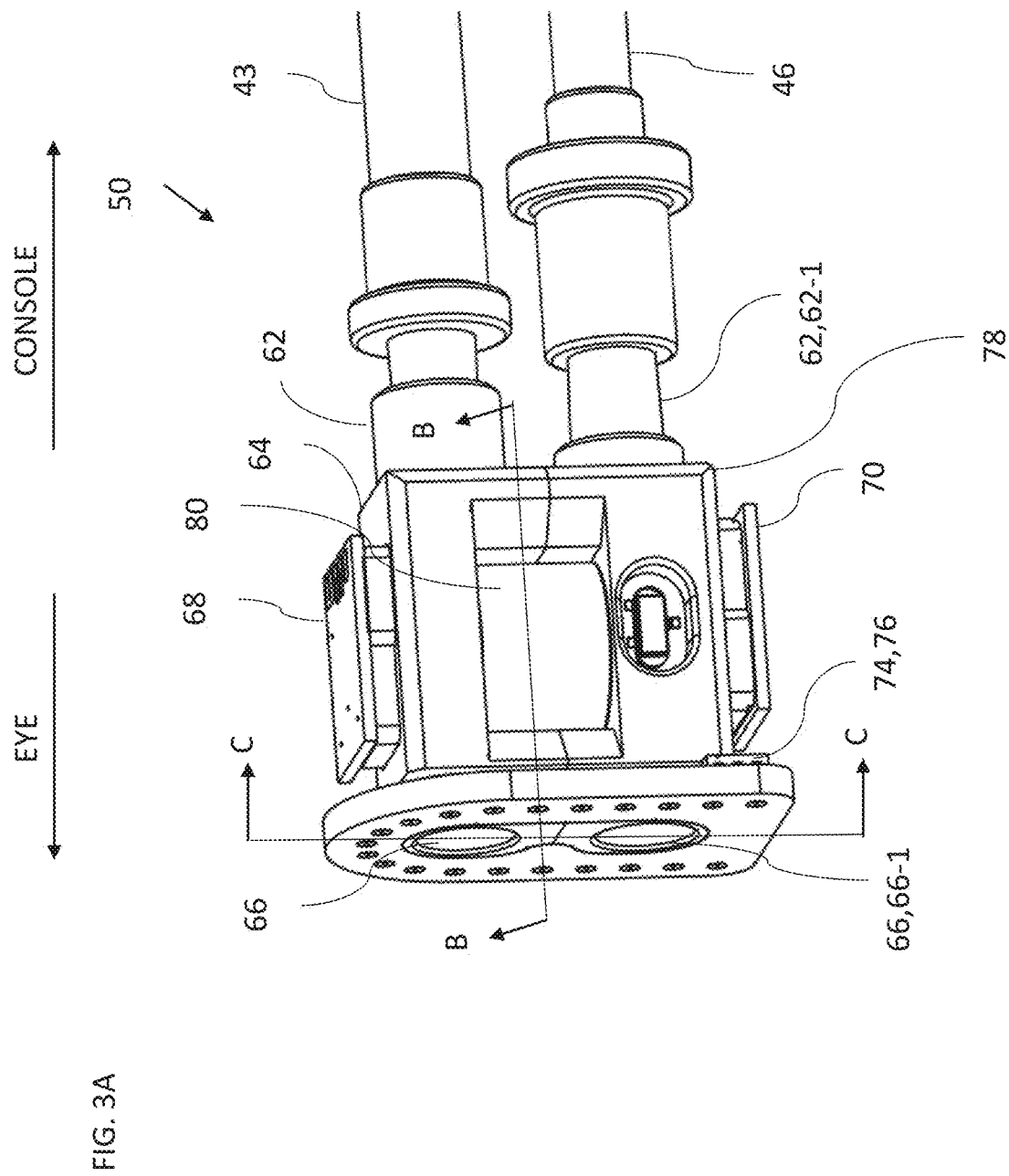
FIG. 3A is a schematic view of an interior of a fluid dynamics cartridge for use in the probe of FIGS. 2A-B.
Figure 3B:
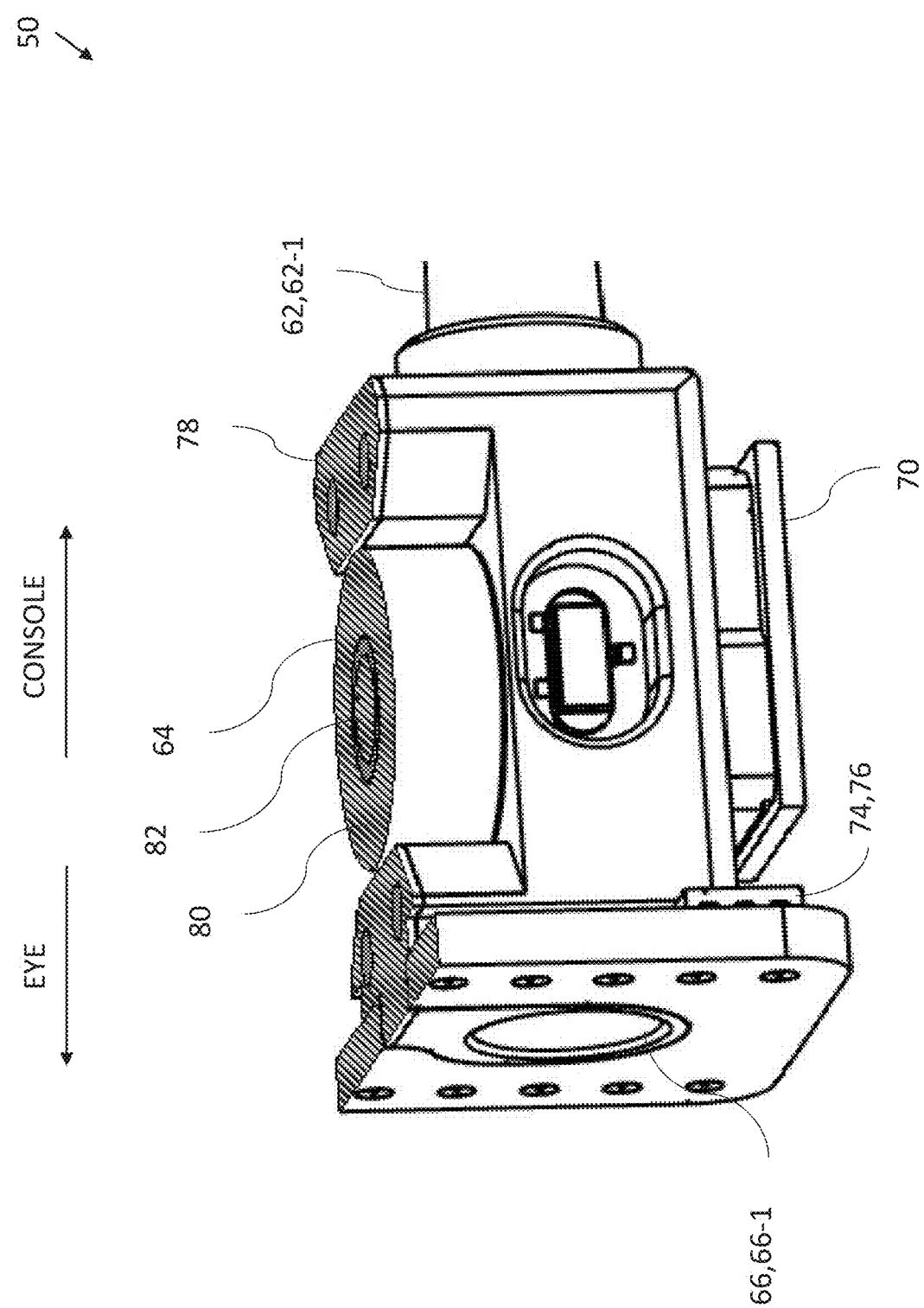
FIG. 3B is a cross-section of the fluid dynamics cartridge through line B:B of FIG. 3A.
Figure 3C:
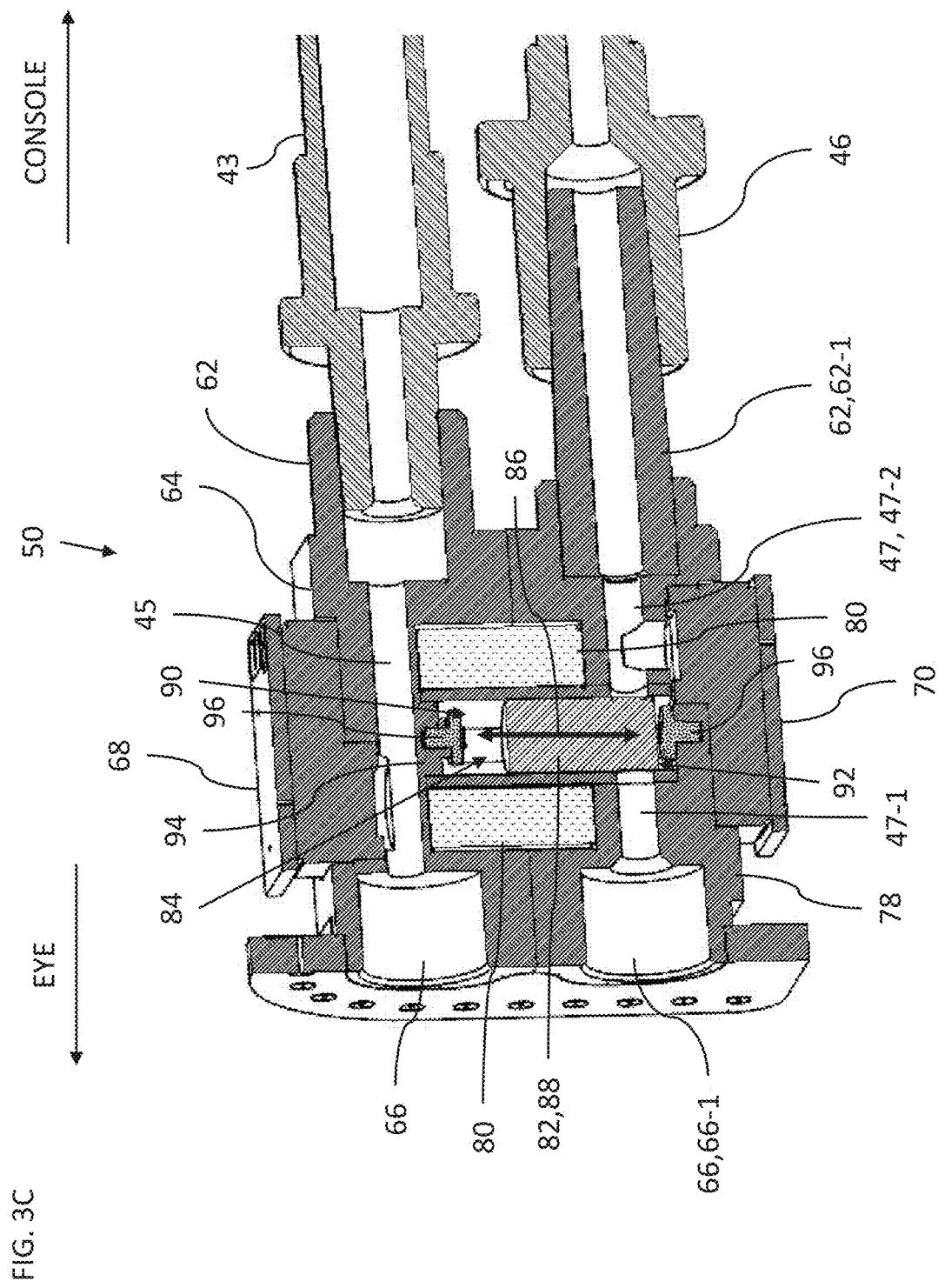
FIG. 3C is a cross-section of the fluid dynamics cartridge through line C:C of FIG. 3A.

Reference is now made to FIGS. 3A-C. FIG. 3A is a schematic view of an interior of a fluid dynamics cartridge 50 for use in the phacoemulsification probe 12 of FIGS. 2A-B. FIG. 3B is a cross-section of the fluid dynamics cartridge 50 through line B:B of FIG. 3A. FIG. 3C is a cross-section of the fluid dynamics cartridge 50 through line C:C of FIG. 3A.

The phacoemulsification probe 12 may include sensors 68, and 70 (which may be pressure sensors), and a solenoid valve 64. In some embodiments, the cartridge 50 includes:

the solenoid valve 64, which includes ports 62 for connection to the irrigation tubing line 43 and aspiration tubing line 46, ports 66 for connection to the ports 60 (FIG. 2B), and sections of the irrigation channel 45 and aspiration channel 47; the sensor 68 connected to the irrigation channel 45; and the sensor 70 connected to aspiration channel 47 on the console 28 side of the solenoid valve 64 (as shown in FIG. 3C). The sensor 68 and the sensor 70 are configured to provide respective signals indicative of respective fluid metrics (e.g., pressure levels) in the irrigation channel 45 and in the aspiration channel 47. The aspiration channel 47 traverses the solenoid valve 64.

Including the sensors 68, 70 in the cartridge 50 may provide higher sensitivity to local changes in fluid dynamics and provide a higher degree of control of the pressure in the eye.

The phacoemulsification probe 12 may include a controller 74 to receive the signal(s) from the pressure sensor 68 and/or the pressure sensor 70, and control the fluid connectivity in the irrigation channel 45 and/or the aspiration channel 47 by selectively opening and closing the solenoid valve 64, responsively to the received signal(s). In some embodiments, the cartridge 50 may also include the controller 74 and/or a memory 76 (e.g., EEPROM) to hold calibration settings and/or a usage counter to count usage of the cartridge 50 and thereby prevent overuse of the cartridge 50. In some embodiments, the controller 74 may be included in the console 28 (FIG. 1). In some embodiments, the functionality of the controller 74 may be performed by the controller 38. Including the controller 74 in the cartridge 50 may allow the controller to be configured for the calibration of the solenoid valve 64. Additionally, or alternatively, including the controller 74 in the cartridge 50 allows the controller to be close to the sensors 68, 70 which may be providing analog signals that could degrade if the signals needed to travel over the cable 33 to the console 28 in which the controller 74 may otherwise be installed.

The cartridge 50 is compact and may be any suitable size. In some embodiments, the cartridge 50 may fit into a cube of 2.5 cm sides.

The aspiration channel 47 includes a section 47-1 coupled with an inlet port 66-1 and a section 47-2 coupled with an outlet port 62-1 (as shown in FIG. 3C). The controller 74 is configured to control the fluid connectivity in the aspiration channel 47 between the inlet port 66-1 and the outlet port 62-1 by selectively opening and closing the solenoid valve 64, responsively to a fluid metric (e.g., pressure level) in the aspiration channel 47. It should be noted that when the solenoid valve 64 is closed, the sensor 70 shown in FIG. 3C is configured to sense a fluid metric (e.g., pressure level) in the section 47-2 between the solenoid valve 64 and the console 28.

The solenoid valve 64 and its operation is now described in more detail. The solenoid valve 64 includes a valve body 78, a solenoid coil 80, and a plunger 82.

Reference is now made to FIG. 3C. The valve body 78 includes the ports 62, the ports 66, a valve cavity 84 having a direction of elongation 86 and configured to provide fluid connectivity between respective ones of the ports 62, 66 (e.g., between the inlet port 66-1 and outlet port 62-1). The solenoid coil 80 is disposed in the valve body 78 around valve cavity 84. The plunger 82 includes a permanent magnet 88. The permanent magnet 88 may comprise all of, or only part of, the plunger 82. For example, the plunger 82 may include the permanent magnet 88 coated or covered with a material of low friction. The plunger 82 is configured to move back-and-forth along the direction of elongation 86 between a position 90 and a position 92 in the valve cavity 84 selectively controlling the fluid connectivity between respective ones of the ports 62, 66 (e.g., between the inlet port 66-1 and outlet port 62-1).

The plunger 82 may have any suitable size, for example, a length in the range of 3 mm to 2 cm (e.g., 6 mm) and a diameter in the range of 1 mm to 1 cm (e.g., 3 mm). The valve body 78 may include a spacer 94 described in more detail with reference to FIGS. 5A-B below. The valve body 78 may also include one or more dampers 96 to soften banging of the plunger 82 against the valve body 78. In FIG. 3C, the upper damper 96 forms part of the spacer 94.

The controller 74 (FIGS. 3A-B) is configured to apply at least one current to the solenoid coil 80 to selectively move the plunger 82 between the position 90 and the position 92, and to selectively maintain the plunger in the position 90 and the position 92, as described below in more detail with reference to FIGS. 5A-B.

Figure 4B:
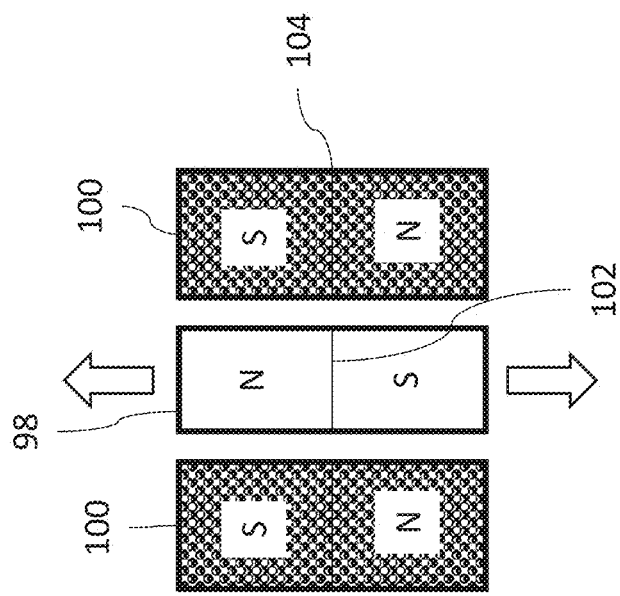
FIGS. 4A-B are schematic views of a permanent magnet in a solenoid coil.
Figure 4A:
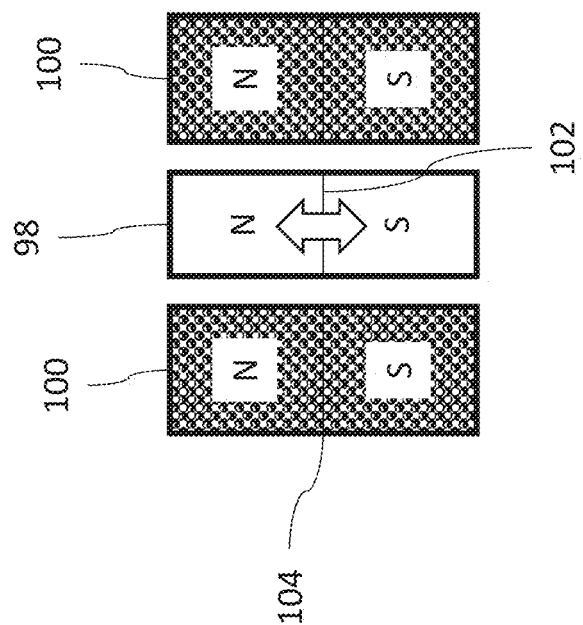

Reference is now made to FIGS. 4A-B, which are schematic views of a permanent magnet 98 in a solenoid coil 100.

In the configuration of FIG. 4A, the polarity of the solenoid coil 100 is in the same direction as the polarity of the permanent magnet 98. In such a configuration, if a center 102 of the permanent magnet 98 is moved a little away from a center 104 of the solenoid coil 100, the permanent magnet 98 will oscillate around the center 104 of the solenoid coil 100 until the permanent magnet 98 settles so that the center 102 of the permanent magnet 98 is aligned with the center 104 of the solenoid coil 100. The permanent magnet 98 therefore rests in a stable position with respect to the solenoid coil 100.

In the configuration of FIG. 4B, the polarity of the solenoid coil 100 is in the opposite direction to the polarity of the permanent magnet 98. In such a configuration, if the center 102 of the permanent magnet 98 is moved a little away from the center 104 of the solenoid coil 100, the permanent magnet 98 will continue to move in that direction. The permanent magnet 98 in FIG. 4B is therefore in an unstable position with respect to the solenoid coil 100.

Figure 5A:
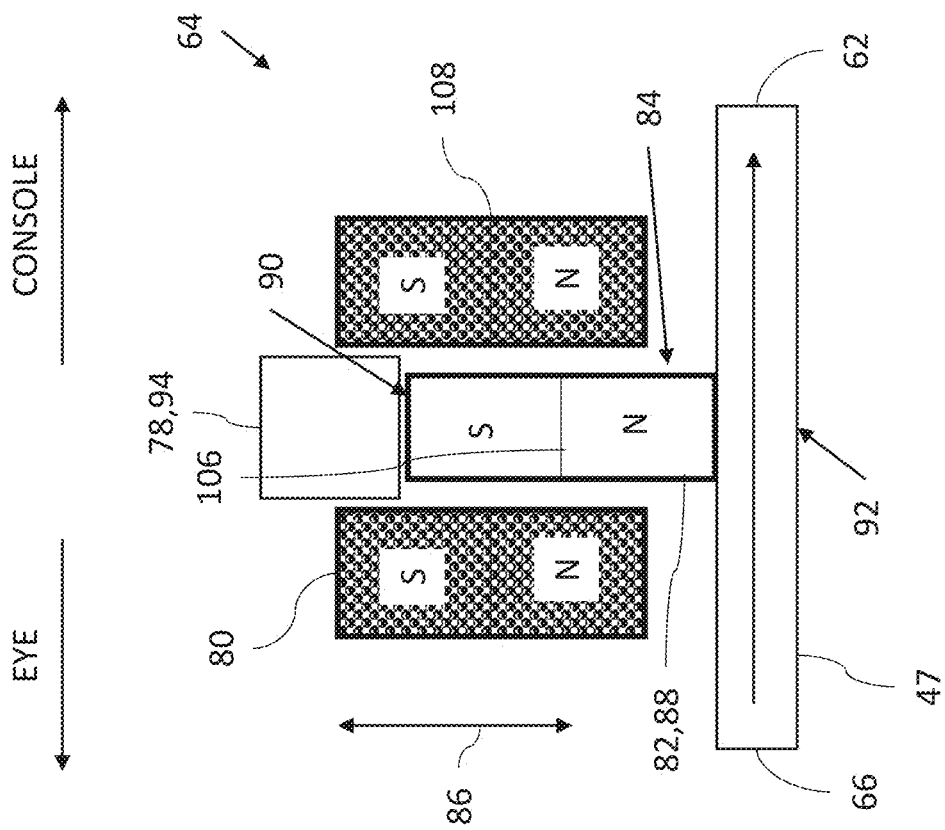
FIGS. 5A-B are schematic views of operation of a solenoid valve for use in the cartridge of FIGS. 3A-C.
Figure 5B:
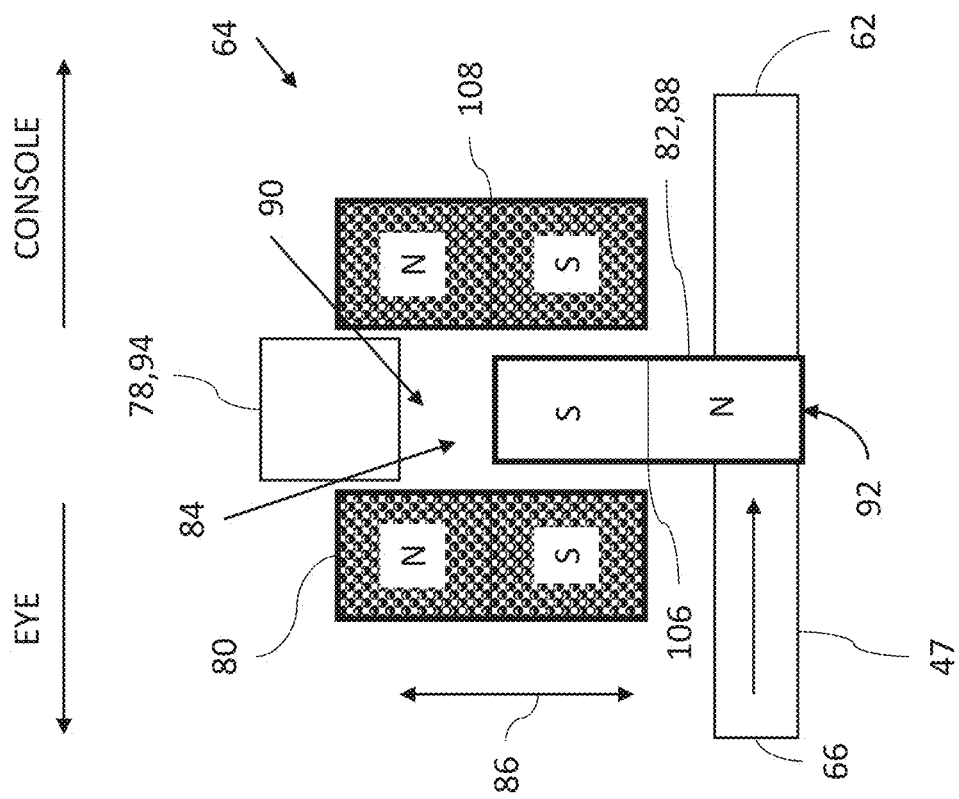

Reference is now made to FIGS. 5A-B, which are schematic views of operation of the solenoid valve 64 for use in the cartridge 50 of FIGS. 3A-C.

The plunger 82 is configured to move back-and-forth along the direction of elongation 86 between position 92 and position 90 in the valve cavity 84 selectively controlling the fluid connectivity between respective ones of the ports 66, 62. The controller 74 (FIGS. 3A-B) is configured to apply current to the solenoid coil 80 to selectively move the plunger 82 between the position 92 and position 90, and to selectively maintain the plunger in the position 92 and position 90. FIG. 5A shows the plunger 82 in position 92 blocking fluid connectivity in the aspiration channel 47. FIG. 5B shows the plunger 82 in position 90 allowing fluid connectivity in the aspiration channel 47.

The plunger 82 does not have a fixed rest position in the valve cavity 84. Even though in some orientations the plunger 82 may fall in one of the positions 92, 94 due to gravity, if the solenoid valve 64 is orientated differently the plunger 84 may fall to a different position. The plunger 82 does not include a restoring element (e.g., spring) configured to restore the plunger 82 to a fixed rest position. The plunger will not always remain in the position 92 or position 90 (e.g., if the orientation of the phacoemulsification probe 12 is changed) without applying current to the solenoid coil 80. In other words, for the solenoid valve 64 to function correctly, a current is applied to the solenoid coil 80 whether the solenoid valve 64 is to remain open or closed. The plunger 82 will remain in the position 90 or the position 92 upon application of current to the solenoid coil 80.

The controller 74 is configured to apply a current to the solenoid coil 80 to activate the solenoid coil 80 with a polarity to cause the plunger 82 to move and be maintained in the position 92 as shown in FIG. 5A. The controller 74 is configured to apply an opposite current to the solenoid coil 80 to activate the solenoid coil 80 with an opposite polarity to cause the plunger 82 to move and be maintained in the position 90 as shown in FIG. 5B.

The permanent magnet 88 has a center 106 with respect to the direction of elongation 86. The solenoid coil 80 has a center 108 with respect to the direction of elongation 86.

The valve body 78 includes the spacer 94 to prevent the center 106 of the magnet 88 moving in the direction of elongation 86 past the center 108 of the solenoid coil 80. Therefore, the spacer 94 maintains asymmetry between the center 108 of the solenoid coil 80 and the center 106 of the permanent magnet 88 with respect to the direction of elongation 86 so that the centers 106, 108 are never aligned with respect to the direction of elongation 86. The above asymmetry is desirable to allow movement of the permanent magnet 88 within the valve cavity 84 to be controlled and the maintained position of the permanent magnet 88 at the position 90 to be stable (as explained above with reference to FIGS. 4A-B). When plunger 82 is in position 90, plunger 82 abuts spacer 94 (see FIG. 5B).

Reference is now made to FIG. 6, which is a flowchart 200 including steps in an exemplary method of operation of system 10 of FIG. 1. Reference is also made to FIG. 3C.

The controller 74 is configured to apply (block 202) a current to the solenoid coil 80 to activate the solenoid coil 80 with a polarity to cause the plunger 82 to move and be maintained in the position 90 so that the solenoid valve 64 is open (and kept open) and there is fluid connectivity along the aspiration channel 47.

The controller 74 is configured to selectively control (block 204) the fluid connectivity responsively to a measured metric in the phacoemulsification probe 12. In some embodiments, the controller 74 is configured to selectively control the fluid connectivity responsively to a sensed fluid flow or pressure from the one or more sensors 68, 70 coupled with aspiration channel 47. The step of block 204 is now described in more detail with reference to sub-steps of blocks 206-230.

The controller 74 is configured to receive a signal indicative of the fluid metric (e.g., pressure level) in the aspiration channel 47 from the sensor 70 (block 206). The controller 74 is configured to detect a rate of change of the fluid metric (e.g., pressure level) in the aspiration channel 47 responsively to the received signal (block 208). At a decision block 210, the controller 74 is configured to determine if the rate of change passes (e.g., exceeds) a given rate of change. If the rate of change does not pass (e.g., exceed) the given rate of change (branch 212), the method returns to the sub-step of block 206. If the rate of change passes (e.g., exceeds) the given rate of change (branch 214), the controller 74 is configured to reduce the fluid connectivity (block 216) between the inlet port 66-1 and the outlet port 62-1. The sub-step of block 216 may include the controller 74 being configured to apply a current to the solenoid coil 80 to activate the solenoid coil 80 with an opposite polarity to cause the plunger 82 to move and be maintained in the position 92 (block 218). The solenoid valve 64 is closed and kept closed thereby blocking fluid connectivity in the aspiration channel 47 at the location of the plunger 82 thereby isolating the eye from the aspiration tubing line 46 (FIG. 1) and protecting the eye from a vacuum surge.

In some embodiments, rather than the solenoid valve 64 closing completely and fast, the solenoid valve 64 may be controlled to close partially and/or slowly. In some embodiments, the activation of the solenoid valve 64 may also be controlled according to pressure, flow, temperature, or a combination of these type of sensed parameters.

The controller 74 is configured to reduce the vacuum in the aspiration tubing line 46 (block 220) (and the portion of the aspiration channel 47 between the solenoid valve 64 and the aspiration tubing line 46), for example, by reducing the action of the pumping sub-system 26, or opening a vent in the aspiration tubing line 46 or in the aspiration channel 47. The controller 74 is configured to detect the fluid metric (e.g., pressure level) in the aspiration channel 47 responsively to signal received from the pressure sensor 70 (block 222). At a decision block 224, the controller 74 is configured to determine if the fluid metric (e.g., pressure level) passes (e.g., exceeds) a given value (e.g., given pressure level). If the fluid metric (e.g., pressure level) does not pass (e.g., exceed) the given value (e.g., given pressure level) (branch 226), the sub-step of block 220 is repeated. If the fluid metric (e.g., pressure level) passes (e.g., exceeds) the given value (e.g., pressure level) (branch 228), the controller 74 is configured to increase (block 230) the fluid connectivity between the inlet port 66-1 and the outlet port 62-1 responsively to the fluid metric (e.g., pressure level) passing (e.g., exceeding) a given value (e.g., given pressure level), for example, the step of block 202 is repeated.

Figure 7:
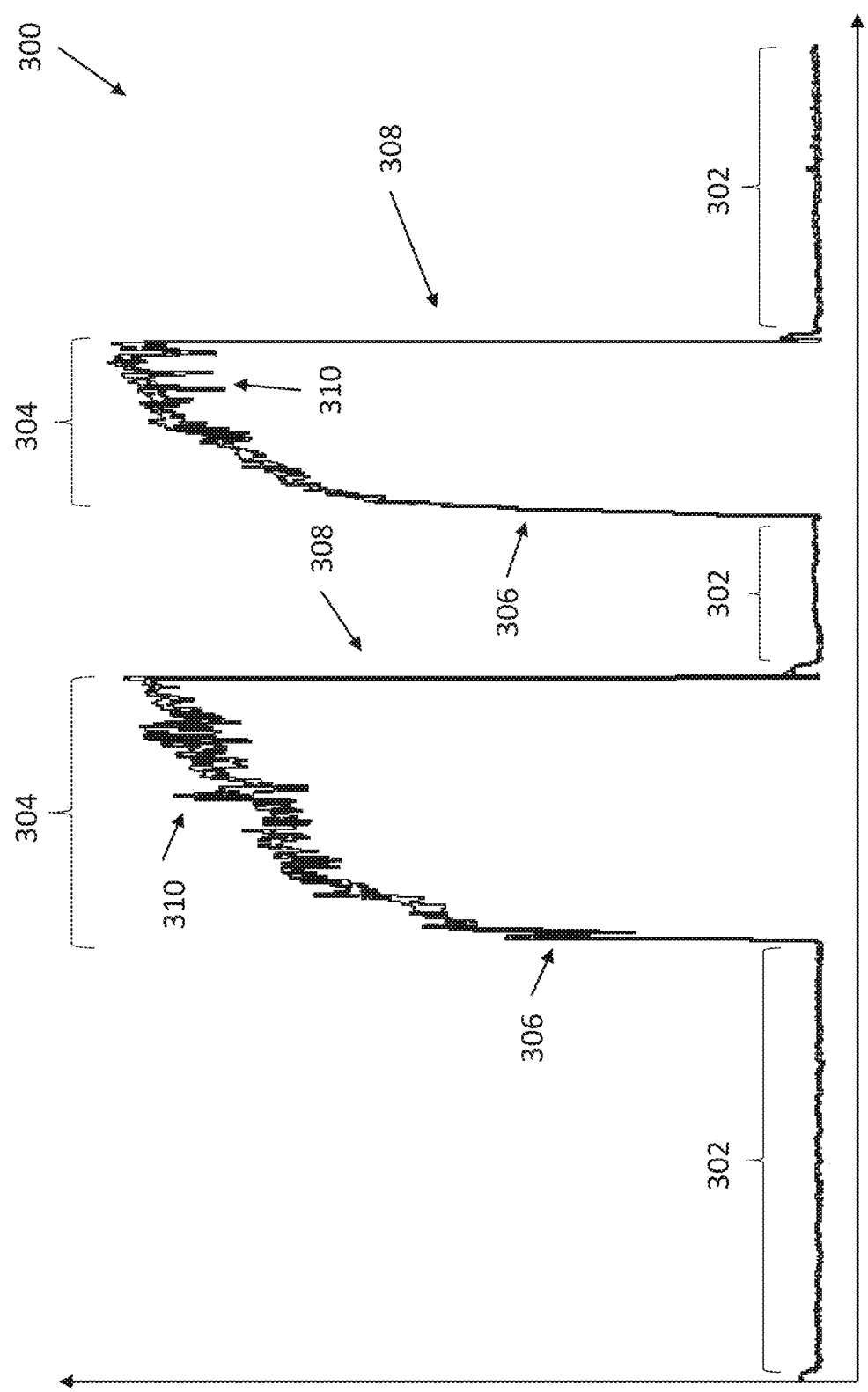
FIG. 7 is a graph of negative pressure against time for use in the system of FIG. 1.

Reference is now made to FIG. 7, which is a graph 300 of negative pressure (e.g., vacuum level) against time for use in the system 10 of FIG. 1. The y-axis of the graph 300 represents negative pressure so as values in the graph 300 move upward pressure decreases.

As previously mentioned, the AVS system is generally constantly operational, and closes the solenoid valve 64 on detection of a given rate of change in pressure (or other fluid metric) even if the phacoemulsification needle 16 is not being vibrated and there is a low risk associated with the needle damaging the eye 20. The constant operation of the AVS system may however be undesirable when the physician is trying to build up a vacuum in the aspiration line 53 as fast as possible, for example, to grab a particle, even when the phacoemulsification needle 16 is not vibrating. Therefore, in some embodiments the valve 64 is only activated (e.g., according to a given change (e.g., given rate of change) in pressure or other fluid metric) during a time period when the needle 16 is being vibrated thereby allowing such activities as the physician to build up a vacuum in the aspiration line 53 as fast as possible, for example, to grab a particle when the phacoemulsification needle 16 is not vibrating.

There may be a general data disconnection between the activation of the needle 16 and the operation of the AVS system such that direct feedback regarding the needle operation may not be available to the AVS system. Therefore, in some embodiments, vibration of the needle 16 may be detected indirectly. When the needle 16 is being vibrated, the needle 16 causes cavitation (bubbles) in the aspirated fluid. The cavitation leads to high frequency pressure fluctuations in the aspiration line 53. The vibration of the needle 16 may therefore be detected according to the level of cavitation in the aspiration line 53. In some embodiments, the cavitation is detected based on detecting pressure fluctuations (above a given threshold) in the aspiration line 53. The pressure level in the aspiration line 53 may be sensed by a pressure sensor, such as the pressure sensor 70.

In some embodiments, high frequency pressure fluctuations in the aspiration line 53 indicative of cavitation may be detected by computing a signal to noise ratio (SNR) of (a window of) the pressure signal provided by the sensor 70. If the SNR is greater than a given threshold, for example, the noise power is greater than 5% of the signal power, the needle 16 may be assumed to be vibrating causing cavitation. FIG. 7 shows regions 302 without much noise or high-frequency pressure fluctuations, and regions 304 with considerable noise or high-frequency pressure fluctuations. The regions 302 are indicative of when the needle 16 is not being vibrated and the regions 304 are indicate of when the needle 16 is being vibrated causing cavitation which in turn leads to high frequency pressure fluctuations in the fluid of the aspiration line 53. Inclines 306 of the graph 300 may indicate respective vacuums being built up by a physician in order to grab hold of the lens or lens particles prior to vibration of the needle 16. Declines 308 of the graph 300 may indicate the release of the vacuums after a period of emulsification. Sharp changes 310 in pressure during vibration of the needle may indicate an occlusion or post-occlusion surge.

In some embodiments, the AVS system is active, and the solenoid valve 64 is closed in response to detecting a change in a fluid metric sensed by the sensor 70, when the needle 16 is being vibrated, for example, at sharp changes 310 of regions 304, but not in regions 302. In particular, the AVS system is not active during the inclines 306.

Control of the AVS system in response to vibration of the needle 16 is described in more detail with reference to FIG. 8 below.

Figure 8:
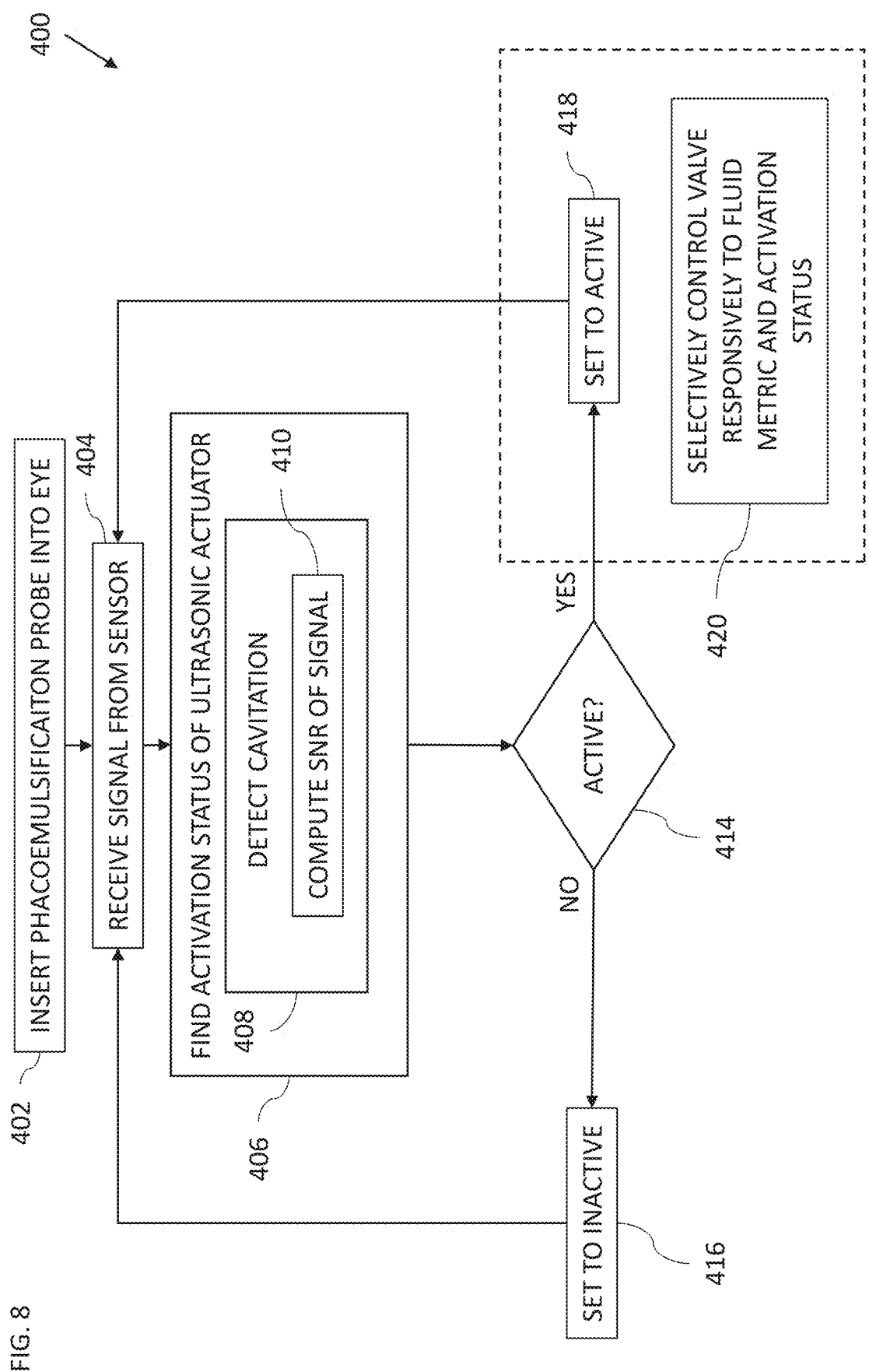
FIG. 8 is a flowchart including steps in a method of operation of the system of FIG. 1.

Reference is now made to FIG. 8, which is a flowchart 400 including steps in a method of operation of the system 10 of FIG. 1. The method described with reference to FIG. 8 refers to solenoid valve 64. The method may be implemented using any suitable valve disposed in the aspiration line 53 and configured to control fluid connectivity in the aspiration line 53. For example, the valve may be comprised in cartridge 50, or at any suitable location in the phacoemulsification probe 12, or external to the phacoemulsification probe 12 at any suitable location along the aspiration line 53, or used with a probe not including the cartridge 50.

The method described with reference to FIG. 8 refers to sensor 70. The method may be implemented using any suitable sensor configured to provide a signal indicative of a fluid metric in the aspiration line 53. The fluid metric may be a pressure metric and/or a flow metric, for example. The sensor may be disposed in the cartridge 50 or at any other suitable location in the phacoemulsification probe 12 or other suitable probe, or externally to the phacoemulsification probe 12 at any suitable location along the aspiration line 53, or used with a probe not including the cartridge 50. The sensor may be disposed adjacent to the valve, e.g., in the cartridge 50, or away from the valve. The sensor 70 may include a pressure sensor configured to sense a pressure metric in the aspiration line 53. Additionally, or alternatively, the sensor 70 may include a flow sensor to sense a speed of flow of fluid in the aspiration line 53.

The controller 38 used in the method described with reference to FIG. 8 may be disposed in the console 28 or in the cartridge 50 or at any suitable location.

The phacoemulsification probe 12 is inserted into the eye 20 (block 402). The controller 38 is configured to receive (a time window of) the signal from the sensor 70 (block 404). The controller 38 is configured to find an activation status of the ultrasonic actuator 52 (block 406). In other words, if needle 16 is vibrating, the ultrasonic actuator 52 is assumed to be active, and if the needle 16 is not vibrating, the ultrasonic actuator 52 is assumed to be inactive. The step of block 406 may include sub-steps described below with reference to the steps of blocks 408-410.

In some embodiments, the controller 38 is configured to detect cavitation caused by vibration of the needle 16 responsively to the signal provided by the sensor 70 (block 408) and find the activation status of the ultrasonic actuator 52 responsively to detecting the cavitation. If cavitation (above a threshold) is detected, then the ultrasonic actuator 52 is assumed to be active. Otherwise, the ultrasonic actuator 52 is assumed to be inactive. In some embodiments, the controller 38 is configured to detect the cavitation caused by the vibration of the needle 16 responsively to pressure fluctuations sensed by the pressure sensor 70 as described in more detail with reference to the step of block 410. A time window of the signal provided by the sensor 70 may be sampled periodically, for example, every 10-200 milliseconds. The time window may have any suitable value, for example, in a range from 5-100 milliseconds. In some embodiments, the signal may be sampled without gaps so that successive time windows of the signal are sampled to detect cavitation. For example, a time window of 20 milliseconds of the signal is sampled, and then another time window (adjacent to the previous time window) of 20 millisecond of the signal may be sampled and so on. In some embodiments, the time windows may overlap.

In some embodiments, the controller 38 is configured to compute a signal-to-noise ratio responsively to (the time window of) the signal provided by the sensor 70 (block 410), and detect the cavitation responsively to the computed signal-to-noise ratio. The signal-to-noise ratio may be computed for each sampled time window, for example, every 10-200 milliseconds.

If the SNR is greater than a given threshold, for example, the noise power is greater than 5% of the signal power, the needle 16 may be assumed to be vibrating causing cavitation. In some embodiments, the (time window of the) signal provided by the sensor 70 may be processed by the controller 38 to provide a pressure signal of pressure against time. The controller 38 then computes the signal-to-noise ratio responsively to the pressure signal.

At a decision block 414, the controller 38 determines if the ultrasonic actuator 52 is active based on the step of block 406. If the controller 38 determines that the ultrasonic actuator 52 is inactive, the controller 38 sets a status to inactive (block 416) and deactivates the AVS system (if currently active) and continues with the step of block 404. If the controller 38 determines that the ultrasonic actuator 52 is active, the controller 38 sets a status to active (block 418) and activates the AVS system (if currently inactive) and continues with the step of block 404.

While the AVS system is active, the controller 38 is configured to selectively control the valve 64 responsively to the fluid metric (block 420). In other words, the controller 38 is configured to selectively control the valve 64 responsively to the fluid metric and the activation status of the ultrasonic actuator 52. The valve 64 may be controlled responsively to the fluid metric using any suitable algorithm, for example, using the method described with reference to the flowchart 200 of FIG. 6.

In some embodiments, the controller 38 is configured to selectively control the valve 64 to restrict fluid flow along the aspiration line 53 responsively to the fluid metric and the activation status of the ultrasonic actuator 52. In some embodiments, the controller 38 is configured to selectively control the valve 64 to restrict fluid flow along the aspiration line 53 responsively to the activation status of the ultrasonic actuator 53 being equal to active and the fluid metric being indicative of an occlusion or a post-occlusion surge. In some embodiments, the controller 38 is configured to selectively control the valve 64 to restrict fluid flow along the aspiration line 53 responsively to the activation status of the ultrasonic actuator being equal to active and a rate of change of the pressure metric in the aspiration line 53 exceeding a threshold value.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification system, comprising:
   a phacoemulsification probe configured to be inserted into an eye, and comprising a needle, a horn configured to support the needle, and an ultrasonic actuator coupled with the horn and configured to vibrate the needle to emulsify a lens of the eye;
   an aspiration line partially disposed in the needle;
   a valve disposed in the aspiration line and configured to control fluid connectivity in the aspiration line;
   a sensor configured to provide a signal indicative of a fluid metric in the aspiration line; and
   a controller configured to:
   detect cavitation caused by vibration of the needle responsively to the signal provided by the sensor;
   find an activation status of the ultrasonic actuator responsively to detecting the cavitation;
   selectively control the valve responsively to the fluid metric and the activation status of the ultrasonic actuator.

2. The system according to claim 1, wherein the controller is configured to selectively control the valve to restrict fluid flow along the aspiration line responsively to the fluid metric and the activation status of the ultrasonic actuator.

3. The system according to claim 1, wherein the controller is configured to selectively control the valve to restrict fluid flow along the aspiration line responsively to the activation status of the ultrasonic actuator being equal to active and the fluid metric being indicative of an occlusion or a post-occlusion surge.

4. The system according to claim 1, wherein the fluid metric is a pressure metric; and the sensor includes a pressure sensor configured to sense the pressure metric in the aspiration line.

5. The system according to claim 4, wherein the controller is configured to selectively control the valve to restrict fluid flow along the aspiration line responsively to the activation status of the ultrasonic actuator being equal to active and a rate of change of the pressure metric in the aspiration line exceeding a threshold value.

6. The system according to claim 1 wherein:
   the sensor includes a pressure sensor configured to sense pressure in the aspiration line; and
   the controller is configured to detect the cavitation caused by the vibration of the needle responsively to pressure fluctuations sensed by the pressure sensor.

7. The system according to claim 6, wherein the controller is configured to:
   compute a signal-to-noise ratio responsively to the signal provided by the sensor; and
   detect the cavitation responsively to the computed signal-to-noise ratio.

8. The system according to claim 7, wherein the controller is configured to detect the cavitation responsively to the computed signal-to-noise ratio exceeding a given threshold value.

9. The system according to claim 6, wherein the controller is configured to selectively control the valve to restrict fluid flow along the aspiration line responsively to the activation status of the ultrasonic actuator being equal to active and a rate of change of the pressure metric sensed by the pressure sensor exceeding a threshold value.

10. A phacoemulsification method, comprising:
    inserting a phacoemulsification probe into an eye;
    removing fluid and waste matter from the eye via an aspiration line partially disposed in a needle of the phacoemulsification probe;
    detecting a signal indicative of a fluid metric in the aspiration line; and
    controlling fluid connectivity in the aspiration line using a valve, wherein the controlling fluid connectivity comprises:
    finding an activation status of an ultrasonic actuator which selectively vibrates the needle;
    selectively controlling the valve responsively to the fluid metric and the activation status of the ultrasonic actuator; and
    detecting cavitation caused by vibration of the needle responsively to the signal provided by the sensor, and wherein the finding includes finding the activation status of the ultrasonic actuator responsively to detecting the cavitation.

11. The method according to claim 10, wherein the selectively controlling includes selectively controlling the valve to restrict fluid flow along the aspiration line responsively to the fluid metric and the activation status of the ultrasonic actuator.

12. The method according to claim 10, wherein the selectively controlling includes selectively controlling the valve to restrict fluid flow along the aspiration line responsively to the activation status of the ultrasonic actuator being equal to active and the fluid metric being indicative of an occlusion or a post-occlusion surge.

13. The method according to claim 10, wherein the fluid metric is a pressure metric, the method further comprises sensing the pressure metric in the aspiration line.

14. The method according to claim 13, wherein the selectively controlling includes selectively controlling the valve to restrict fluid flow along the aspiration line responsively to the activation status of the ultrasonic actuator being equal to active and a rate of change of the pressure metric in the aspiration line exceeding a threshold value.

15. The method according to claim 10, further comprising sensing pressure in the aspiration line, and wherein the detecting includes detecting the cavitation caused by the vibration of the needle responsively to sensed pressure fluctuations.

16. The method according to claim 15, further comprising computing a signal-to-noise ratio responsively to the provided signal, and wherein the detecting the cavitation includes detecting the cavitation responsively to the computed signal-to-noise ratio.

17. The method according to claim 16, wherein the detecting the cavitation includes detecting the cavitation responsively to the computed signal-to-noise ratio exceeding a given threshold value.

18. The method according to claim 15, wherein the selectively controlling includes selectively controlling the valve to restrict fluid flow along the aspiration line responsively to the activation status of the ultrasonic actuator being equal to active and a rate of change of a sensed pressure metric exceeding a threshold value.

\* \* \* \* \*